United States Patent
Meller et al.

(10) Patent No.: US 11,173,028 B1
(45) Date of Patent: Nov. 16, 2021

(54) POSITIONING A MEDICAL DEVICE IN THE RIGHT ATRIUM OR RIGHT VENTRICLE USING A NON-FLEXIBLE CATHETER

(71) Applicant: Cardiac Implants LLC, Tarrytown, NY (US)

(72) Inventors: Nimrod Meller, Kfar Yehoshua (IL); David Alon, Zichron Yaacov (IL)

(73) Assignee: Cardiac Implants LLC, Tarrytown, NY (US)

(*) Notice: Subject to any disclaimer, the term of this patent is extended or adjusted under 35 U.S.C. 154(b) by 0 days.

(21) Appl. No.: 17/191,136

(22) Filed: Mar. 3, 2021

Related U.S. Application Data

(60) Provisional application No. 63/076,023, filed on Sep. 9, 2020.

(51) Int. Cl.
*A61F 2/24* (2006.01)
*A61B 17/00* (2006.01)

(52) U.S. Cl.
CPC ...... *A61F 2/2427* (2013.01); *A61B 17/00234* (2013.01); *A61B 2017/00243* (2013.01); *A61B 2017/00292* (2013.01); *A61F 2/2466* (2013.01)

(58) Field of Classification Search
None
See application file for complete search history.

(56) References Cited

U.S. PATENT DOCUMENTS

| | | | | |
|---|---|---|---|---|
| 5,558,644 A | * | 9/1996 | Boyd | A61M 1/3653 604/102.02 |
| 5,810,746 A | * | 9/1998 | Goldstein | A61B 10/06 600/585 |
| 6,540,782 B1 | * | 4/2003 | Snyders | A61F 2/2418 623/2.11 |
| 8,430,926 B2 | | 4/2013 | Kirson | |
| 9,180,005 B1 | * | 11/2015 | Lashinski | A61F 2/2445 |
| RE46,126 E | | 8/2016 | Kirson | |
| RE46,127 E | | 8/2016 | Kirson | |
| 9,517,130 B1 | | 12/2016 | Alon et al. | |
| 10,143,553 B2 | | 12/2018 | Alon et al. | |
| 10,206,776 B2 | | 2/2019 | Alon | |
| 10,357,364 B2 | | 7/2019 | Alon | |
| 10,398,555 B2 | | 9/2019 | Alon et al. | |
| 10,500,049 B2 | | 12/2019 | Alon | |
| 10,575,952 B2 | | 3/2020 | Alon | |
| 10,667,913 B2 | | 6/2020 | Alon et al. | |
| 10,695,179 B2 | | 6/2020 | Alon | |
| 10,716,670 B2 | | 7/2020 | Alon | |

(Continued)

*Primary Examiner* — Shaun L David
(74) *Attorney, Agent, or Firm* — Potomac Law Group, PLLC

(57) ABSTRACT

A device can be introduced into the right atrium of a subject's heart by introducing the distal end of a hollow, straight, and stiff shaft into the subject's right internal jugular vein, and advancing the distal end of the shaft into the right atrium via the superior vena cava. The position of the distal end of the shaft is adjusted by manipulating a handle affixed to a portion of the shaft that remains outside the subject's body. The handle can be used to rotate the shaft about its longitudinal axis, rotate the shaft about an anterior-posterior axis, rotate the shaft about a medial-lateral axis, and/or advance the shaft in the caudal direction. A device is advanced through the interior of the shaft until the device extends beyond the distal end of the shaft and into the right atrium.

20 Claims, 5 Drawing Sheets

(56) References Cited

U.S. PATENT DOCUMENTS

| | | | |
|---|---|---|---|
| 10,786,356 B2 | 9/2020 | Alon | |
| 10,881,390 B2 | 1/2021 | Modesitt et al. | |
| 10,893,940 B2 | 1/2021 | Alon et al. | |
| 2005/0222488 A1* | 10/2005 | Chang | A61B 17/0401 600/37 |
| 2006/0241745 A1* | 10/2006 | Solem | A61F 2/246 623/2.18 |
| 2010/0249915 A1* | 9/2010 | Zhang | A61F 2/2418 623/2.11 |
| 2012/0316641 A1* | 12/2012 | Jonsson | A61F 2/2445 623/2.11 |
| 2014/0379006 A1* | 12/2014 | Sutherland | A61F 2/2487 606/151 |
| 2016/0022961 A1* | 1/2016 | Rosenman | A61M 25/0141 604/95.04 |
| 2017/0079790 A1* | 3/2017 | Vidlund | A61F 2/2418 |
| 2017/0156861 A1* | 6/2017 | Longoria | A61F 2/2457 |
| 2018/0071094 A1 | 3/2018 | Alon | |
| 2018/0071095 A1 | 3/2018 | Alon et al. | |
| 2018/0133009 A1 | 5/2018 | Alon | |
| 2018/0289473 A1* | 10/2018 | Rajagopal | A61F 2/2418 |
| 2018/0303609 A1* | 10/2018 | Kenny | A61F 2/2436 |
| 2019/0038411 A1 | 2/2019 | Alon | |
| 2019/0053905 A1 | 2/2019 | Alon | |
| 2019/0201198 A1 | 7/2019 | Modesitt | |
| 2019/0201199 A1 | 7/2019 | Modesitt | |
| 2019/0216603 A1* | 7/2019 | Orlov | A61B 17/12036 |
| 2020/0121458 A1* | 4/2020 | Vidlund | A61F 2/2436 |
| 2020/0155316 A1 | 5/2020 | Alon | |
| 2020/0163769 A1 | 5/2020 | Alon | |
| 2020/0229926 A1 | 7/2020 | Alon | |
| 2021/0085461 A1 | 3/2021 | Neumark et al. | |

\* cited by examiner

POSITIONING A MEDICAL DEVICE IN THE RIGHT ATRIUM OR RIGHT VENTRICLE USING A NON-FLEXIBLE CATHETER

CROSS REFERENCE TO RELATED APPLICATIONS

This application claims the benefit of U.S. Provisional Application 63/076,023 filed Sep. 9, 2020, which is incorporated herein by reference in its entirety.

BACKGROUND

Transcatheter delivery of cardiac medical devices (e.g., replacement valves, devices for reducing the size of an annulus, etc.) typically rely on flexible catheters to route the device to the place where it will be installed. First, the flexible catheter is introduced into the subject's vasculature, and the distal end of the catheter is advanced until it reaches the general vicinity where the device will be deployed. The flexibility of the catheter's shaft provides "trackability" of the catheter through the tortuous anatomy between the access point and the target site. Subsequently, the device is extended out of the distal end of the catheter, and a steering mechanism is used to reposition the device before the device is deployed. These steering mechanisms typically have at least two degrees of freedom (e.g., up/down plus right/left) to improve the maneuverability of the device prior to deployment.

SUMMARY OF THE INVENTION

One aspect of the invention is directed to a first method of performing a procedure in a right atrium of a subject's heart. The first method comprises (a) introducing a distal end of a hollow, straight, and stiff shaft into the subject's right internal jugular vein; and (b) advancing the distal end of the shaft into the subject's right atrium via the subject's right brachiocephalic vein and the subject's superior vena cava. At least a portion of the shaft remains outside the subject's body after the distal end of the shaft is advanced into the subject's right atrium. The first method also comprises (c) advancing a device in a caudal direction through an interior of the shaft so that the device is positioned in the subject's right atrium and extends caudally beyond the distal end of the shaft; and (d) adjusting a position of the distal end of the shaft by manipulating a handle affixed to the portion of the shaft that remains outside the subject's body. The manipulating of the handle results in at least two of (i) rotating the shaft about a longitudinal axis of the shaft, (ii) rotating the shaft about an anterior-posterior axis, (iii) rotating the shaft about a medial-lateral axis, and (iv) advancing the shaft in the caudal direction.

In some instances of the first method, a bending member extends distally beyond the distal end of the shaft. The bending member is configured to bend with only a single degree of freedom in response to movement of a control surface, and the method further comprises moving the control surface to further adjust the position of the bending member.

In some instances of the first method, the device that extends caudally beyond the distal end of the shaft is configured to bend with only a single degree of freedom in response to movement of a control surface. In these instances, the method further comprises moving the control surface to further adjust the position of the device that extends caudally beyond the distal end of the shaft.

In some instances of the first method, the device that extends caudally beyond the distal end of the shaft is configured to assume a pre-bent shape upon exiting the distal end of the shaft. In some instances of the first method, the anterior-posterior axis is less than 2 cm away from the subject's clavicle bone, and the medial-lateral axis is less than 2 cm away from the subject's clavicle bone.

In some instances of the first method, the manipulating of the handle results in at least three of (i) rotating the shaft about the longitudinal axis of the shaft, (ii) rotating the shaft about the anterior-posterior axis, (iii) rotating the shaft about the medial-lateral axis, and (iv) advancing the shaft in the caudal direction.

In some instances of the first method, the device comprises a device for reducing a diameter of a tricuspid anulus. In some instances of the first method, the device comprises a replacement for a tricuspid valve. In some instances of the first method, the device comprises a clip for clipping leaflets of a tricuspid valve. In some instances of the first method, the shaft has an outer diameter of less than 7.5 mm. In some instances of the first method, the shaft has an outer diameter of 5.5-7.5 mm. In some instances of the first method, the shaft has an inner diameter of at least 5 mm. In some instances of the first method, the shaft has metal sidewalls with no openings in the sidewalls. In some instances of the first method, the shaft has stainless steel sidewalls with no openings in the sidewalls.

Another aspect of the invention is directed to a second method of performing a procedure in a right side of a subject's heart. The second method comprises (a) introducing a distal end of a hollow, straight, and stiff shaft into the subject's right internal jugular vein; and (b) advancing the distal end of the shaft into the subject's superior vena cava via the subject's right brachiocephalic vein. At least a portion of the shaft remains outside the subject's body after the distal end of the shaft is advanced into the subject's superior vena cava. The second method also comprises (c) advancing a device in a caudal direction through an interior of the shaft so that the device extends caudally beyond the distal end of the shaft; and (d) adjusting a position of the distal end of the shaft by manipulating a handle affixed to the portion of the shaft that remains outside the subject's body. The manipulating of the handle results in at least one of (i) rotating the shaft about a longitudinal axis of the shaft, (ii) rotating the shaft about an anterior-posterior axis, (iii) rotating the shaft about a medial-lateral axis, and (iv) advancing the shaft in the caudal direction.

Some instances of the second method further comprise advancing the distal end of the shaft into the subject's right atrium after step (b) and prior to step (c), wherein at least a portion of the shaft remains outside the subject's body after the distal end of the shaft is advanced into the subject's right atrium.

In some instances of the second method, a bending member extends distally beyond the distal end of the shaft, and the bending member is configured to bend with only a single degree of freedom in response to movement of a control surface. In these instances, the method further comprises moving the control surface to further adjust the position of the bending member.

In some instances of the second method, the device that extends caudally beyond the distal end of the shaft is configured to bend with only a single degree of freedom in response to movement of a control surface, and the method further comprises moving the control surface to further adjust the position of the device that extends caudally beyond the distal end of the shaft.

In some instances of the second method, the manipulating of the handle results in at least three of (i) rotating the shaft about the longitudinal axis of the shaft, (ii) rotating the shaft about the anterior-posterior axis, (iii) rotating the shaft about the medial-lateral axis, and (iv) advancing the shaft in the caudal direction. In some of these instances, the anterior-posterior axis is less than 2 cm away from the subject's clavicle bone, and the medial-lateral axis is less than 2 cm away from the subject's clavicle bone.

In some instances of the second method, the device comprises a device for reducing a diameter of a tricuspid anulus. In some instances of the second method, the device comprises a replacement for a tricuspid valve. In some instances of the second method, the device comprises a clip for clipping leaflets of a tricuspid valve.

Another aspect of the invention is directed to a first apparatus that comprises a hollow, straight, and stiff metal shaft and a handle. The shaft has a longitudinal axis and an outer diameter between 5.5 and 7.5 mm, an inner diameter of at least 5 mm, and the shaft has metal sidewalls with no openings in the sidewalls. The handle is affixed to the shaft and has a distal end. The shaft extends distally beyond the distal end of the handle by between 30 and 70 cm, and the handle is affixed to the shaft such that manipulation of the handle can (i) rotate the shaft about the longitudinal axis of the shaft, (ii) rotate the shaft about an anterior-posterior axis, (iii) rotate the shaft about a medial-lateral axis, (iv) advance the shaft in a caudal direction, and (v) withdraw the shaft in a cranial direction. The first apparatus further comprises a device for (a) reducing a diameter of a tricuspid anulus, (b) replacing a tricuspid valve, or (c) clipping leaflets of a tricuspid valve, and the device is disposed in a collapsed state within an interior of the shaft. The device is configured to be advanced in the caudal direction through the interior of the shaft until the device extends caudally beyond the distal end of the shaft.

In some embodiments of the first apparatus, the shaft extends distally beyond the distal end of the handle by between 40 and 60 cm. In some embodiments of the first apparatus, the device is further configured so that after the device has been extended caudally beyond the distal end of the shaft, the device can bend with only a single degree of freedom in response to movement of a control surface.

Some embodiments of the first apparatus further comprise a hollow bending member that extends distally beyond the distal end of the shaft, and the bending member is configured to bend with only a single degree of freedom in response to movement of a control surface.

In some embodiments of the first apparatus, the device is a device for reducing a diameter of a tricuspid anulus. In some embodiments of the first apparatus, the device is a device for replacing a tricuspid valve. In some embodiments of the first apparatus, the device is a device for clipping leaflets of a tricuspid valve.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Many procedures require the use of flexible catheters to route a device to its desired position in the heart. For example, pacemaker leads are often routed into an access site in the left subclavian vein or the left axillary vein and advanced through the vasculature until they reach their destination in one or more chambers of the heart. Similarly, replacement valves are often routed through the femoral artery and the aorta, and advanced through the vasculature until they reach their destination. In these situations, the catheter must be flexible so that it can bend around any curves in the vasculature that lie between the access point and the destination.

There is, however, one anatomic path to the heart that does not require the use of a flexible catheter to reach a destination in the heart. More specifically, when a catheter is introduced into an access site in the right internal jugular vein, the path between the access site and the right atrium will be relatively straight. In this situation, it becomes possible to use a stiff shaft (which serves as a catheter) to reach a desired destination in the heart (e.g., in the right atrium). And notably, when a stiff shaft is used, the position of the distal end of the shaft can be adjusted by simply manipulating a handle that is affixed to the portion of the shaft that remains outside the subject's body. After the distal end of the shaft is in the desired position, another device is advanced through the shaft and used to treat the heart. Examples of such devices include but are not limited to replacement valves, devices that reduce the size of a valve annulus, a clip for grasping leaflets of a cardiac valve, spacers or replacement valves, devices for chordal repair within the right ventricle, annuloplasty rings, devices for ablation of the right atrium, septal closure devices, shunts, etc.

Figure 1:
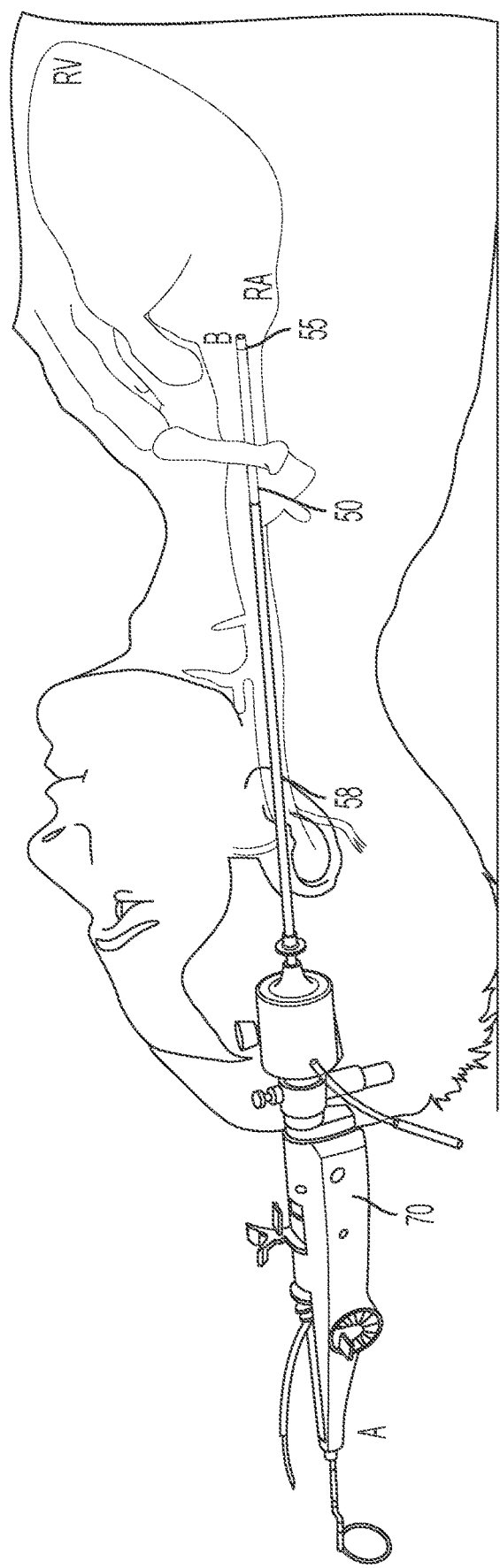
FIG. 1 depicts a stiff-shaft delivery system that can be used to introduce a device into the right atrium of a subject's heart.

FIGS. 1-5 depict an example of using this approach to bring a device that reduces the size of a valve annulus into position adjacent to the tricuspid valve. (A description of such a device can be found in U.S. Pat. Nos. 10,206,776 and 10,357,364, each of which is incorporated herein by reference.) More specifically, FIG. 1 shows how the right atrium of a subject's heart is accessed by introducing the distal end 55 of a shaft 50 into the subject's right internal jugular vein (above the subclavian branch). The shaft is hollow, straight, and stiff. Next, the distal end of the shaft 50 is advanced into the subject's right atrium via the subject's right brachiocephalic vein and the subject's superior vena cava. A portion 58 of the shaft 50 remains outside the subject's body after the distal end 55 of the shaft is advanced into the subject's right atrium.

When the distal end 55 of the shaft 50 is positioned in the subject's right atrium, the shaft 50 will pass directly posterior of the clavicle bone and adjacent tissue. As a result, the clavicle bone and the adjacent tissue will serve as a hinge point or a fulcrum for certain types of motions.

Figure 2:
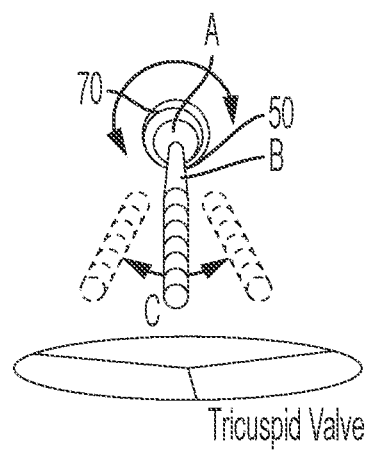
FIG. 2 shows how the FIG. 1 embodiment can be rotated about a longitudinal axis of the shaft.
Figure 3:
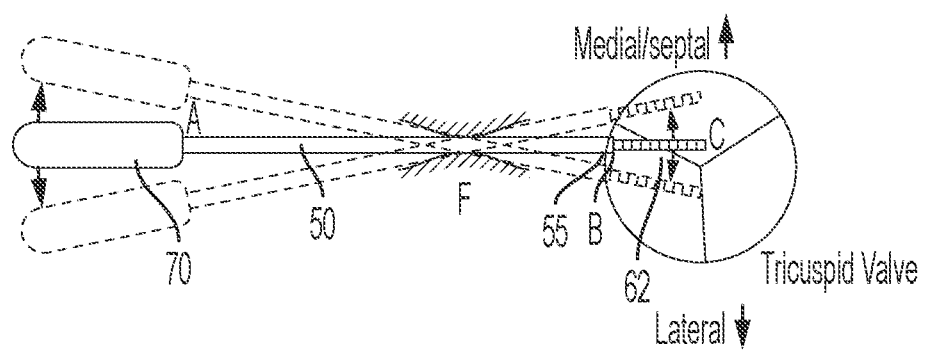
FIG. 3 shows how the distal end of the FIG. 1 embodiment can be moved in the lateral or medial directions by moving the handle.
Figure 4:
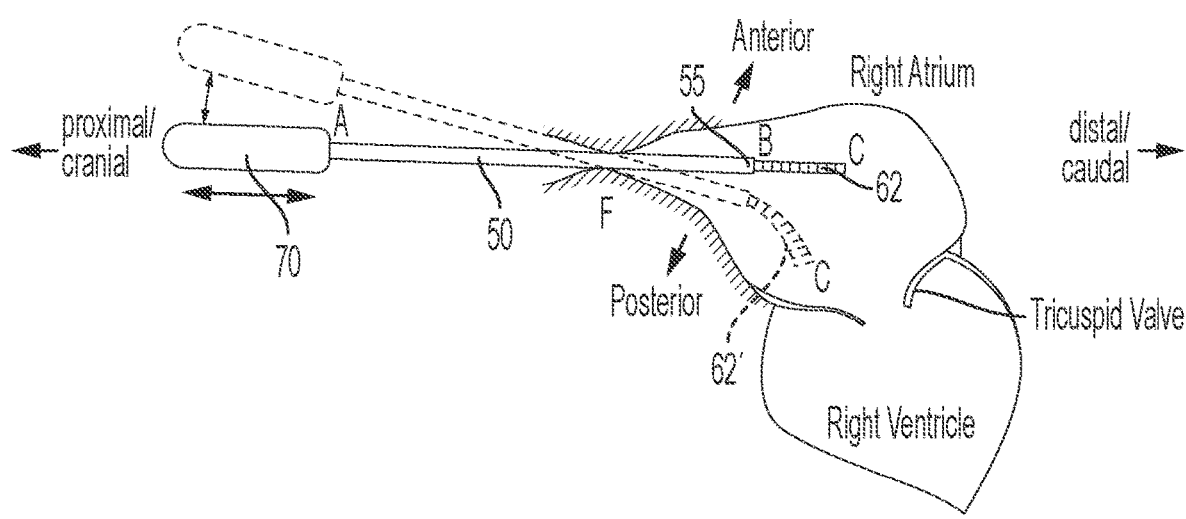
FIG. 4 shows how the distal end of the FIG. 1 embodiment can be moved in the anterior or posterior directions by moving the handle.

When the shaft 50 is in this position, manipulation operations that are possible using the handle 70 include the following: (i) rotating the handle 70 in order to rotate the shaft 50 about a longitudinal axis of the shaft, as depicted in FIG. 2; (ii) moving the handle in a medial or lateral direction, which results in rotating the shaft about an anterior-posterior axis that is positioned near the fulcrum F and is perpendicular to the page in FIG. 3, which in turn causes the distal end 55 of the shaft 50 to move in a lateral or medial direction (as depicted in FIG. 3), (iii) moving the handle in an anterior or posterior direction, which results in rotating the shaft about a medial-lateral axis that is positioned near the fulcrum F and is perpendicular to the page in FIG. 4, which in turn causes the distal end 55 of the shaft 50 to move in a posterior or anterior direction (as depicted in FIG. 4); (iv) advancing the handle 70 in the caudal direction, which causes the distal end 55 of the shaft 50 to move in the caudal direction; and (v) moving the handle 70 in the cranial direction, which causes the distal end 55 of the shaft 50 to move in the cranial direction (as depicted in FIG. 4). As used herein, "stiff" means sufficiently stiff to achieve manipulation operations (ii) and (iii) listed above.

Typically, the location of the anterior-posterior axis described in the previous paragraph will be less than 2 cm away from the subject's clavicle bone, and the medial-lateral axis described in the previous paragraph will be less than 2 cm away from the subject's clavicle bone.

Note that the extent of movement of the distal end 55 of the shaft 50 that is possible in the medial or lateral directions (see FIG. 3) and in the anterior or posterior directions (see FIG. 4) will be limited by the anatomy of the clavicle bone and the surrounding tissue, which acts as a fulcrum or hinge about which the shaft 50 rotates.

Figure 5:
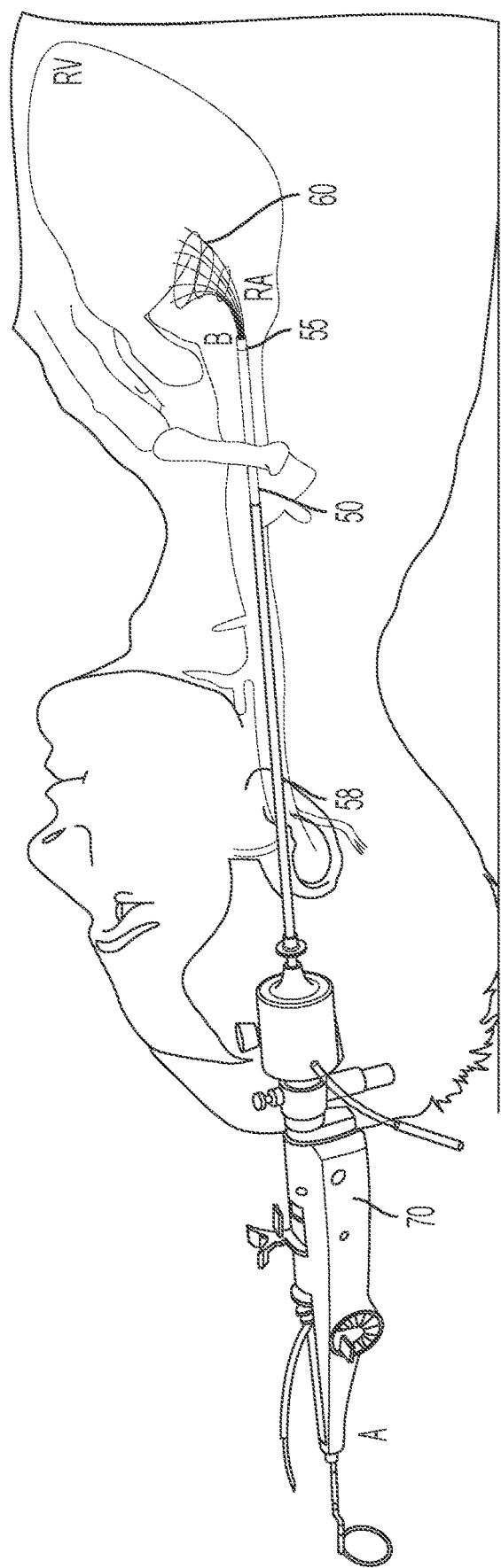
FIG. 5 depicts an example of introducing a device into the right atrium of a subject's heart using the FIG. 1 stiff shaft delivery system.

FIG. 5 shows how, once the distal end 55 of the shaft 50 has been moved into the right atrium, the distal end 55 of the shaft 50 serves as an access port within the right atrium through which devices can be introduced, or through which therapies can be applied. For example, a catheter that delivers a device 60 can be introduced via the interior of the shaft 50, and advanced in a caudal direction through the hollow interior of the shaft 50 until the device 60 extends caudally beyond the distal end 55 of the shaft 50 and moves into the right atrium. The device 60 may subsequently be moved in and out, rotated, and/or deflected (with respect to the shaft 50) until the device 60 reaches the desired target anatomy within the right atrium (e.g., the tricuspid valve).

In addition, after the device 60 has been extended beyond the distal end 55 of the shaft 50, the position of the device 60 can also be adjusted by manipulating the handle 70 (which is affixed to the portion of the shaft 50 that remains outside the subject's body) using any of the manipulation operations (i) through (v) described above. And because the shaft 50 is stiff, moving the handle 70 will result in a corresponding movement of the distal end 55 of the shaft 50, which will move the device 60.

When accessing a patient's vasculature via the jugular vein, it is advantageous for the diameter of the device that is introduced into the jugular vein to be as small as possible. Since catheter-based devices that can bend with only a single degree of freedom can generally be made smaller in diameter than devices that can bend with more than one degree of freedom, it can be advantageous to design the device 60 (which is introduced via the interior of the shaft 50 until it extends caudally beyond the distal end 55 of the shaft) to bend with only a single degree of freedom (e.g., in response to movement of a control surface, not shown). In this case, even though the bending mechanism has only a single degree of freedom, the device 60 can still be maneuvered to its intended destination by combining the movements of the distal end 55 of the shaft 50 described above (including rotating the shaft 50 about the longitudinal axis of the shaft) with the bending ability of the device 60.

Taking this concept one step further, the device 60 (which is introduced via the interior of the shaft 50) can be designed to assume a pre-bent configuration when it extends caudally beyond the distal end 55 of the shaft (e.g., by forming part of the device 60 from a shape memory alloy of such as nitinol). This alternative can be used to achieve a further reduction in the diameter of the device 60, because there is no need to incorporate a bending mechanism into the design of the device 60. In this case, even though the bending profile of the device 60 that extends caudally beyond the distal end 55 of the shaft 50 is not adjustable, it may still be possible to maneuver the device 60 to its desired location by combining the movements of the distal end 55 of the shaft 50 described above with controlling how far the device 60 extends caudally beyond the distal end 55 of the shaft 50.

Preferably, the shaft has an outer diameter of less than 7.5 mm, and more preferably the shaft has an outer diameter of 5.5-7.5 mm. Preferably, the shaft has an inner diameter of at least 5 mm. Preferably, the shaft has metal (e.g., stainless steel) sidewalls with no openings in the sidewalls. The shaft should be strong enough so that all of the manipulations (i) through (v) described above can be accomplished without causing plastic deformation of the shaft.

The length of the shaft 50 that extends distally beyond the handle 70 is preferably between 30 and 70 cm, and more preferably between 40 and 60 cm. During use, the shaft includes (a) an internal portion that extends between the access point in the right internal jugular vein and the right atrium plus (b) an external portion that extends between the handle 70 and the access point. This external portion should be long enough to permit maneuverability, but short enough to avoid awkwardness.

Optionally, a hollow bending member 62 that extends distally beyond the distal end 55 of the shaft 50 may be configured to bend with only a single degree of freedom in response to movement of a control surface (not shown). In this situation, the control surface is moved to adjust the position of the bending member using that single degree of freedom (e.g., to move the bending member from the straight position 62 to the bent position 62' depicted in FIG. 4). The bending member 62 may be affixed to the distal end of the shaft 50. Alternatively, a similar bending member configured to bend with only a single degree of freedom may be incorporated into the device 60.

Figure 6:
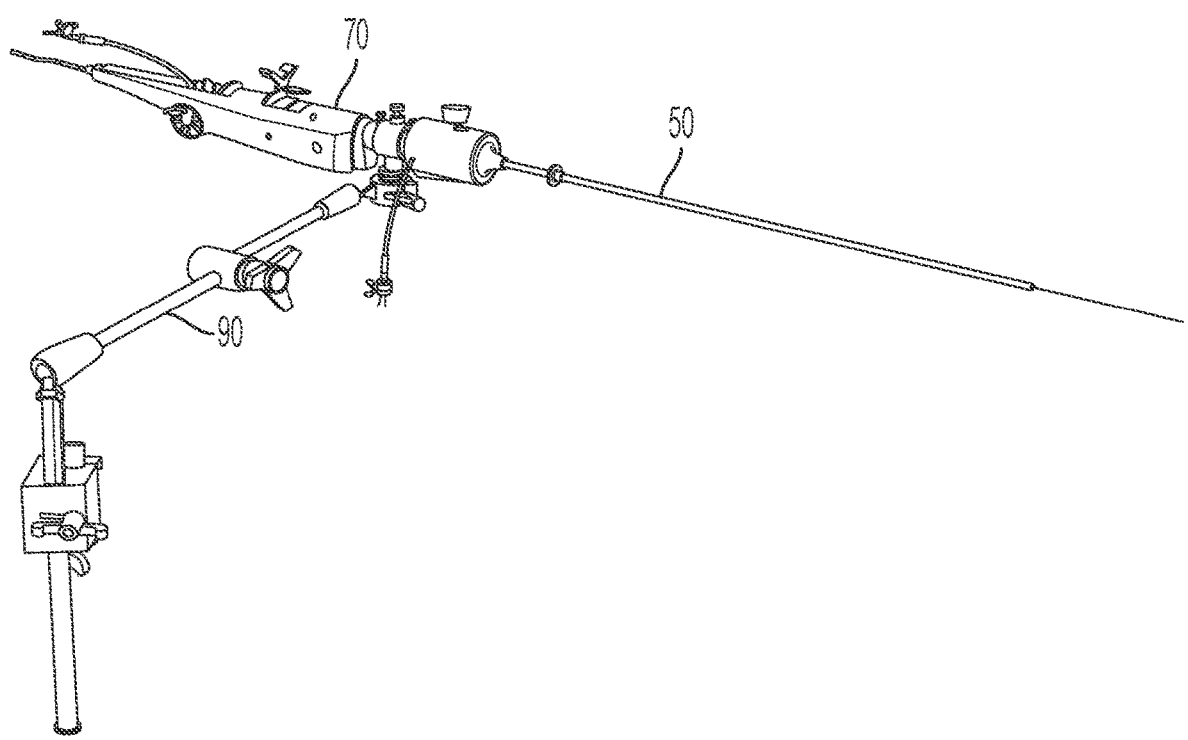
FIG. 6 depicts the FIG. 1 embodiment mounted to a locking articulated arm.

Optionally, after the distal end 55 of the shaft 50 has been moved to a desired location, the shaft may be locked into a fixed position using a locking articulating arm that is fixed with respect to the surface upon which the subject is lying, as depicted in FIG. 6.

Note that in FIG. 1, the device 60 is depicted as being positioned inside the subject's right atrium. But the devices and methods described herein may also be used in the superior vena cava by stopping the movement of the distal end 55 of the shaft 50 when the distal end 55 reaches the superior vena cava, before it enters the right atrium. In addition, because the inferior vena cava is generally aligned with the superior vena cava, the devices and methods described herein may also be used to access the inferior vena cava by extending the distal end 55 of the shaft 50 beyond the right atrium and into the inferior vena cava.

The devices and methods described herein may also be used to access the right ventricle (e.g., to repair chordae) by positioning the distal end 55 of the shaft 50 in the right atrium, then advancing a suitable device through the shaft 50 until it extends caudally beyond the distal end 55 of the shaft, and subsequently advancing and steering that device beyond the tricuspid valve and into the right ventricle. This may be accomplished, for example, using a combination of manipulations of the handle 70 (in order to move the distal end 55 of the shaft to a desired location within the right atrium) plus a steering mechanism (not shown) incorporated into the device.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of performing a procedure in a right atrium of a subject's heart, the method comprising:
   (a) introducing a distal end of a shaft into the subject's right internal jugular vein, wherein the shaft is hollow, straight, and stiff;
   (b) advancing the distal end of the shaft into the subject's right atrium via the subject's right brachiocephalic vein and the subject's superior vena cava, wherein at least a portion of the shaft remains outside the subject's body after the distal end of the shaft is advanced into the subject's right atrium, and wherein the shaft passes directly posterior of the subject's clavicle bone and adjacent tissue so that the clavicle bone and the adjacent tissue serve as a fulcrum;
   (c) advancing a device in a caudal direction through an interior of the shaft so that the device is positioned in the subject's right atrium and extends caudally beyond the distal end of the shaft; and
   (d) adjusting a position of the distal end of the shaft by manipulating a handle affixed to the portion of the shaft that remains outside the subject's body,
   wherein the manipulating of the handle results in at least one of rotating the shaft about an anterior-posterior axis with respect to the fulcrum and rotating the shaft about a medial-lateral axis with respect to the fulcrum.

2. The method of claim 1, wherein a bending member extends distally beyond the distal end of the shaft, wherein the bending member is configured to bend with only a single degree of freedom in response to movement of a control surface, and wherein the method further comprises moving the control surface to further adjust the position of the bending member.

3. The method of claim 1, wherein the device that extends caudally beyond the distal end of the shaft is configured to bend with only a single degree of freedom in response to movement of a control surface, and wherein the method further comprises moving the control surface to further adjust the position of the device that extends caudally beyond the distal end of the shaft.

4. The method of claim 1, wherein the device that extends caudally beyond the distal end of the shaft is configured to assume a pre-bent shape upon exiting the distal end of the shaft.

5. The method of claim 1, wherein the anterior-posterior axis is less than 2 cm away from the subject's clavicle bone, and the medial-lateral axis is less than 2 cm away from the subject's clavicle bone.

6. The method of claim 1, wherein the manipulating of the handle results in at least three of (i) rotating the shaft about the longitudinal axis of the shaft, (ii) rotating the shaft about the anterior-posterior axis with respect to the fulcrum, (iii) rotating the shaft about the medial-lateral axis with respect to the fulcrum, and (iv) advancing the shaft in the caudal direction.

7. The method of claim 1, wherein the device comprises a device for reducing a diameter of a tricuspid anulus.

8. The method of claim 1, wherein the device comprises a replacement for a tricuspid valve.

9. The method of claim 1, wherein the device comprises a clip for clipping leaflets of a tricuspid valve.

10. The method of claim 1, wherein the shaft has an outer diameter of less than 7.5 mm.

11. The method of claim 1, wherein the shaft has an outer diameter of 5.5-7.5 mm.

12. The method of claim 1, wherein the shaft has an inner diameter of at least 5 mm.

13. The method of claim 1, wherein the shaft has metal sidewalls with no openings in the sidewalls.

14. The method of claim 1, wherein the shaft has stainless steel sidewalls with no openings in the sidewalls.

15. A method of performing a procedure in a right side of a subject's heart, the method comprising:
   (a) introducing a distal end of a shaft into the subject's right internal jugular vein, wherein the shaft is hollow, straight, and stiff;
   (b) advancing the distal end of the shaft into the subject's superior vena cava via the subject's right brachiocephalic vein until the distal end of the shaft is caudally beyond the subject's clavicle bone wherein at least a portion of the shaft remains outside the subject's body after the distal end of the shaft is caudally beyond the clavicle bone, and wherein the shaft passes directly posterior of the clavicle bone and adjacent tissue so that the clavicle bone and the adjacent tissue serve as a fulcrum;
   (c) advancing a device in a caudal direction through an interior of the shaft so that the device extends caudally beyond the distal end of the shaft; and
   (d) adjusting a position of the distal end of the shaft by manipulating a handle affixed to the portion of the shaft that remains outside the subject's body,
   wherein the manipulating of the handle results in at least one of rotating the shaft about an anterior-posterior axis with respect to the fulcrum and rotating the shaft about a medial-lateral axis.

16. The method of claim 15, further comprising advancing the distal end of the shaft into the subject's right atrium after step (b) and prior to step (c), wherein at least a portion of the shaft remains outside the subject's body after the distal end of the shaft is advanced into the subject's right atrium.

17. The method of claim 15, wherein a bending member extends distally beyond the distal end of the shaft, wherein the bending member is configured to bend with only a single degree of freedom in response to movement of a control surface, and wherein the method further comprises moving the control surface to further adjust the position of the bending member.

18. The method of claim 15, wherein the device that extends caudally beyond the distal end of the shaft is configured to bend with only a single degree of freedom in response to movement of a control surface, and wherein the method further comprises moving the control surface to further adjust the position of the device that extends caudally beyond the distal end of the shaft.

19. The method of claim 15, wherein the manipulating of the handle results in at least three of (i) rotating the shaft about the longitudinal axis of the shaft, (ii) rotating the shaft about the anterior-posterior axis with respect to the fulcrum, (iii) rotating the shaft about the medial-lateral axis with respect to the fulcrum, and (iv) advancing the shaft in the caudal direction.

20. The method of claim 19, wherein the anterior-posterior axis is less than 2 cm away from the subject's clavicle bone, and the medial-lateral axis is less than 2 cm away from the subject's clavicle bone.

\* \* \* \* \*